(12) United States Patent
Levin et al.

(10) Patent No.: US 10,953,147 B2
(45) Date of Patent: Mar. 23, 2021

(54) ESTIMATION OF THE DRY WEIGHT OF A DIALYSIS PATIENT

(71) Applicants: Fresenius Medical Care Holdings, Inc., Waltham, MA (US); Fresenius Medical Care Deutschland, GMBH, Bad Homburg (DE)

(72) Inventors: Nathan W. Levin, New York, NY (US); Fansan Zhu, Flushing, NY (US); Peter Kotanko, New York, NY (US); Peter Wabel, Darmstadt (DE); Ciro Tetta, Mirandola (IT)

(73) Assignee: Fresenius Medical Care Holdings, Inc., Waltham, MA (US)

(*) Notice: Subject to any disclaimer, the term of this patent is extended or adjusted under 35 U.S.C. 154(b) by 28 days.

(21) Appl. No.: 15/591,973

(22) Filed: May 10, 2017

(65) Prior Publication Data
US 2017/0239408 A1   Aug. 24, 2017

Related U.S. Application Data

(62) Division of application No. 14/345,856, filed as application No. PCT/US2012/055914 on Sep. 18, 2012, now Pat. No. 9,675,294.
(Continued)

(30) Foreign Application Priority Data

Sep. 19, 2011 (WO) ............... PCT/US2011/052152

(51) Int. Cl.
*A61M 1/16* (2006.01)
*A61B 5/0537* (2021.01)
(Continued)

(52) U.S. Cl.
CPC ......... *A61M 1/1611* (2014.02); *A61B 5/0205* (2013.01); *A61B 5/028* (2013.01);
(Continued)

(58) Field of Classification Search
CPC .............. A61B 5/14546; A61B 5/4839; A61B 5/150022; A61B 5/157; A61B 5/4848;
(Continued)

(56) References Cited

U.S. PATENT DOCUMENTS

| 9,675,294 B2 | 6/2017 | Levin et al. |
| 2006/0122540 A1* | 6/2006 | Zhu ...................... A61B 5/0537 600/587 |

(Continued)

FOREIGN PATENT DOCUMENTS

| JP | 2004-49492 A | 2/2004 |
| WO | WO 2011/054693 A1 | 5/2011 |

OTHER PUBLICATIONS

International Search Report and Written Opinion for PCT/US2012/055914 dated Dec. 4, 2012; entitled "Estimation of the Dry Weight of a Dialysis Patient".
(Continued)

*Primary Examiner* — Deborah L Malamud
(74) *Attorney, Agent, or Firm* — Kacvinsky Daisak Bluni, PLLC

(57) ABSTRACT

In an embodiment, the invention relates to methods, apparatus, computer programs and computer program products for estimating a dry weight of a dialysis patient comprising the steps of determining a first fluid status of the patient between treatment sessions in a first stage, determining a second fluid status of the patient during treatment sessions in a second stage and estimating the dry weight based on the second fluid status.

23 Claims, 7 Drawing Sheets

Related U.S. Application Data

(60) Provisional application No. 61/536,488, filed on Sep. 19, 2011.

(51) Int. Cl.

| | | |
|---|---|---|
| *A61B 5/00* | (2006.01) | |
| *A61B 5/0205* | (2006.01) | |
| *A61B 5/0295* | (2006.01) | |
| *A61B 5/1455* | (2006.01) | |
| *A61B 6/00* | (2006.01) | |
| *A61B 8/08* | (2006.01) | |
| *A61B 5/028* | (2006.01) | |
| *A61B 5/145* | (2006.01) | |
| *A61B 5/021* | (2006.01) | |
| *A61B 5/026* | (2006.01) | |
| *A61B 5/08* | (2006.01) | |

(52) U.S. Cl.
CPC .......... *A61B 5/0295* (2013.01); *A61B 5/0537* (2013.01); *A61B 5/1455* (2013.01); *A61B 5/14546* (2013.01); *A61B 5/4839* (2013.01); *A61B 5/4875* (2013.01); *A61B 5/4878* (2013.01); *A61B 6/50* (2013.01); *A61B 8/0891* (2013.01); *A61M 1/16* (2013.01); *A61B 5/021* (2013.01); *A61B 5/0261* (2013.01); *A61B 5/08* (2013.01); *A61B 8/5223* (2013.01); *A61M 2205/3303* (2013.01); *A61M 2205/3317* (2013.01); *A61M 2230/04* (2013.01); *A61M 2230/20* (2013.01); *A61M 2230/65* (2013.01)

(58) Field of Classification Search
CPC ..... A61B 5/14507; A61B 5/4836; A61B 5/03; A61B 5/0537; A61B 5/150992; A61B 5/4875; A61B 5/145; A61B 5/486; A61B 5/015; A61M 1/00; A61M 1/14; A61M 1/1601; A61M 27/002; G06F 19/3418; G06F 19/3468; G06F 19/345
See application file for complete search history.

(56) References Cited

U.S. PATENT DOCUMENTS

| | | | |
|---|---|---|---|
| 2007/0175827 A1* | 8/2007 | Wariar | G16H 20/40 210/645 |
| 2010/0010425 A1 | 1/2010 | Yu et al. | |
| 2010/0076398 A1* | 3/2010 | Scheurer | A61B 5/0215 604/505 |

OTHER PUBLICATIONS

Kotanko, et al. "Current State of Bioimpedeance Techniques in Dialysis", Nephrol Dial Transplant 23:808-812, 2008.

Zhu, et al. "Estimation of Normal Hydration in Dialysis Patients using Whole Body and Calf Biompedance analysis", Physiol. Meas. 32:887-902, Jun. 2011.

* cited by examiner

ESTIMATION OF THE DRY WEIGHT OF A DIALYSIS PATIENT

CROSS-REFERENCE TO RELATED APPLICATION

This application is a divisional of U.S. application Ser. No. 14/345,856, now U.S. Pat. No. 9,675,294, filed Sep. 18, 2012, which is the U.S. National Stage of International Application No. PCT/US2012/055914, filed Sep. 18, 2012, which designates the U.S., published in English, and claims the benefit of U.S. Provisional Application No. 61/536,488 filed Sep. 19, 2011. U.S. application Ser. No. 14/345,856 also claims priority to International Application No. PCT/US2011/052152 filed Sep. 19, 2011. The entire teachings of the above applications are incorporated herein by reference.

FIELD

The present disclosure relates to the estimation of the dry weight of a dialysis patient and bringing an initially fluid-overloaded dialysis patient into a normal fluid status and/or to dry weight. Although of general value, knowledge of an individual's dry weight is especially important for renal patients undergoing dialysis procedures.

BACKGROUND

Fluid status is an important issue in long-term dialysis patients and is related to clinical outcome. In fact, knowledge of a patient's fluid status is essential in efficiently managing hemo- as well as peritoneal-dialysis patients. Chronic fluid overload is associated with left ventricular hypertrophy, left ventricular dilatation, arterial hypertension, and eventually the development of congestive heart failure. High interdialytic weight gain on top of chronic fluid overload further increases the burden for the cardiovascular system. Recent studies have shown that fluid overload can even be linked to an increased mortality (Wizemann V. et al., "The mortality risk of overhydration in haemodialysis patients", Nephrol. Dial. Transplant 2009, 24:1574-1579). Management of the fluid status involves restriction of sodium intake and, to the extent possible and over time, attainment of a post-dialysis weight equal to the patient's dry weight.

The determination, achievement, and maintenance of dry weight are challenging because of the absence of appropriate technologies for estimating dry weight. Consequently, the physician's prescription for the clinical post-dialytic target weight is usually based on clinical indicators and unfortunately is often no more than an informed guess. Fluid overload can be expressed as excess extracellular fluid volume (ECV). In order to have a comparative standard for a reference to body mass, body composition or total body water (TBW) is required.

Dry weight may be defined as the weight at which an individual is as close as possible to a physiological fluid status without experiencing symptoms indicative of fluid overload or deficit. Clinically, dry weight is determined as the lowest weight a patient can tolerate without developing intra- or interdialytic symptoms of hypovolemia. This definition is flawed since it does not take into account patients with myocardial or autonomic system disease in whom symptoms may occur with gross fluid overload, i.e., these patients may exhibit symptoms which would indicate they are at dry weight when, in fact, they are fluid overloaded. Clinical assessment is also hampered by the fact that some liters of fluid may accumulate in the body before edema becomes clinically evident and that it does not account for changes in lean body mass, fat mass or nutritional status over time. Consequently, a majority of dialysis patients may be fluid overloaded with or without specific symptoms.

Various approaches towards a more objective measure of dry weight have been developed, such as blood volume monitoring, ultrasound assessment of inferior vena cava diameter, and several biochemical parameters, such as brain or atrial natriuretic peptide. None of these measures, however, gives a recognized accurate estimate of dry weight due to the fact that they have not been proved to be practical or reliable in the detection of dry weight in individual patients.

Isotope dilution methods are frequently recommended for fluid volume measurement (ECV or TBW), but they are clinically not feasible because of technical complexity and expense. These methods can determine the absolute quantities of ECV and TBW but cannot determine the amount of excess extracellular water (fluid overload) because they do not provide a dry weight value.

Efforts have been made in the past to use bioimpedance technology to facilitate the dry weight prescription process. Sec, for example, Kuhlmann et al., "Bioimpedance, dry weight and blood pressure control: new methods and consequences", Current Opinion in Nephrology and Hypertension, 2005, 14:543-549, the disclosure of which is entirely incorporated by reference.

Several different bioimpedance approaches to determine dry weight have been published:

The normovolemic-hypervolemic slope method (see, e.g. Chamney et al., "A new technique for establishing dry weight in hemodialysis patients via whole body bioimpedance", Kidney Int., 2002, 61:2250-2258, the disclosure of which is entirely incorporated by reference) applies whole body multi-frequency bioimpedance to assess pre-dialytic total body extracellular fluid volume and compares the extracellular fluid volume/body weight relation at hypervolemia with the standard value in normovolemic individuals.

The resistance-reactance graph method (see, e.g. Piccoli et al., "A new method for monitoring body fluid variation by bioimpedance analysis: the RXc graph", Kidney Int., 1994, 46:534-539, the disclosure of which is entirely incorporated by reference) uses whole body single frequency bioimpedance at 50 kHz for assessment of fluid status and nutritional status from height-adjusted resistance and reactance. The resulting resistance-reactance vector is set in relation to a distribution range in a normovolemic population. The difficulty of this method is that it does not provide absolute values of the fluid status—patients can only be compared to percentiles of a normal population.

"Whole body" bioimpedance spectroscopy (wBIS) is a noninvasive technique calculating the whole body extracellular fluid volume (wECV) and the whole body intracellular fluid volume (wICV) by measuring resistance and reactance over a range of alternating current frequencies (e.g. 50 to 250 frequencies from ca. 1 kHz to 1000 kHz). Ratios of wECV or wICV to total body water volume (TBW) or the ratio wECV/wICV are used to assess the fluid status of a patient (Wei Chen et al., "Extracellular Water/Intracellular Water Is a Strong Predictor of Patient Survival in Incident Peritoneal Dialysis Patients", Blood Purif., 2007, 25:260-266, the disclosure of which is entirely incorporated by reference).

The newest and more sophisticated technique is a whole body bioimpedance spectroscopy with a physiological tissue model: wECV and wTBW are measured by whole body bioimpedance spectroscopy and additionally the fluid status and body composition are calculated. This is achieved by setting the measured patient in relation to a subject with a normal fluid status and the same body composition. Thus it relates back to the normohydrated properties of tissue. This physiologic tissue model is described in "A whole-body model to distinguish excess fluid from the hydration of major body tissues", Chamney P. W., Wabel P., Moissl U. M. et al., Am. J. Clin. Nutr., 2007, January, 85(1):80-9, the disclosure of which is entirely incorporated by reference. This method allows the patient specific prediction of the normal fluid status and the normal fluid status weight—the weight, the patient would have with a working kidney. However the accuracy of this method can be influenced by degrees of fluid overload.

An additional method is based on measurement of calf normalized resistivity (CNR) at different fluid status of pre-dialysis or post-dialysis with comparison of the results to a normal population (Zhu F, Kotanko P, Levin W. N. et al., Estimation of Normal Hydration in Dialysis Patients using Whole Body and Calf Bioimpedance Analysis. Physiol. Meas., 2011, 32:887-902, the disclosure of which is entirely incorporated by reference).

A conceptually different method (see, for example, Zhu et al., "Adjustment of dry weight in hemodialysis patients using intradialytic continuous multifrequency bioimpedance of the calf", Int. J. Artif Organs, 2004, 12:104-109 and Zhu et al., "A method for the estimation of hydration state during hemodialysis using a calf bioimpedance technique", Physiol. Meas., 2008: S503-S516, the disclosures of which are entirely incorporated by reference) uses segmental bioimpedance in the form of intradialytic calf bioimpedance to record changes in calf resistance or resistivity which is equivalent to extracellular fluid volume during dialysis (in the following: cBIS). Dry weight determined by this method ($DW_{cBIS}$) is defined as the body weight at which calf extracellular volume is not further reduced despite ongoing ultrafiltration. Although this method is good for estimating $DW_{cBIS}$ of a patient, the technique requires the performance of bioimpedance measurements throughout a dialysis session. Dry weight cannot be predicted by this method. In addition, patient movement at the lower limb is limited during the dialysis session and measuring electrodes have to be kept in place until the session is finished.

Despite the fact that the aforementioned methods are widely used in clinics throughout the world, there exists a need for improved methods for monitoring the fluid status of a fluid-overloaded patient which are easy to implement and/or generate reliable dry weight estimations, in particular when a severely overloaded patient needs to be brought to his/her normal fluid status or dry weight. In other words, it would be beneficial for the adequate fluid management of dialysis patients to quantify fluid overload and to be able to estimate the dry weight more reliably during the reduction of fluid overload than currently done in clinical practice. Furthermore, an urgent need exists for treatment of a patient based on such monitoring in particular to avoid intradialytic symptoms.

SUMMARY

The above deficiencies in the art are addressed by the teaching according to the independent claims. Preferred embodiments are claimed in the dependent claims.

In one embodiment, the present disclosure relates to a method for estimating a dry weight of a patient comprising the steps of determining a first fluid status of the patient between treatment sessions in a first stage, determining a second fluid status of the patient during treatment sessions in a second stage and estimating the dry weight based on the second fluid status.

In one embodiment, the invention relates to a method of bringing an initially fluid-overloaded dialysis patient into his/her normal fluid status comprising the steps of determining a first fluid status of the patient between treatment sessions in a first stage, reducing the fluid overload of the patient based on the first fluid status, deteimining a second fluid status of the patient during treatment sessions in a second stage and reducing the fluid overload of the patient based on the second fluid status.

In one embodiment, the invention relates to a method of bringing an initially fluid-overloaded dialysis patient into his/her normal fluid status, further comprising the step of estimating an absolute fluid status difference between the normal fluid status and the first fluid status, wherein reducing the fluid overload in the first stage is based on the absolute fluid status difference.

In one embodiment, the invention relates to a method of bringing an initially fluid-overloaded dialysis patient into his/her normal fluid status, further comprising the step of estimating the dry weight of the patient based on the second fluid status, wherein reducing the fluid overload of a patient is based on the estimated dry weight.

In one embodiment, the invention relates to a method of bringing an initially fluid-overloaded dialysis patient into his/her normal fluid status, further comprising the step(s) of determining a third fluid status between treatment sessions in a third stage and, optionally, reducing the fluid overload of the patient based on the third fluid status in the third stage.

In one embodiment, the invention relates to a method of bringing an initially fluid-overloaded dialysis patient into his/her normal fluid status, wherein the patient's fluid overload is reduced at most to a level corresponding to an additional loss of 0.5 kg, preferably 0.3 kg, more preferably 0.2 kg and most preferably 0.1 kg of body weight during a dialysis session in the first stage, the second stage and/or the third stage.

In one embodiment, the invention relates to a method for estimating a dry weight of a patient and/or a method of bringing an initially fluid-overloaded patient into his/her normal fluid status, wherein the patient is a dialysis patient and wherein the treatment session is a session of a dialysis treatment.

In one embodiment, the invention relates to a method for estimating a dry weight of a dialysis patient and/or a method of bringing an initially fluid-overloaded dialysis patient into his/her normal fluid status, wherein the first fluid status is determined by a pre-treatment session measurement.

In one embodiment, the invention relates to a method for estimating a dry weight of a dialysis patient and/or a method of bringing an initially fluid-overloaded dialysis patient into his/her normal fluid status, wherein the first fluid status is determined by a post-treatment session measurement.

In one embodiment, the invention relates to a method for estimating a dry weight of a dialysis patient and/or a method of bringing an initially fluid-overloaded dialysis patient into his/her normal fluid status, wherein the first fluid status is determined by at least one of a) a physical examination method, preferably the observation of pedal edema, the measurement of blood pressure and/or the determination of jugular venous pressure, b) an imaging method, preferably chest x-ray imaging and/or inferior vena caval diameter ultrasound imaging, c) biochemical markers, preferably ΔNP, BNP, nT-pro BNP and/or cGMP, d) a thermal dilution determination method, preferably extravascular lung index determination, e) a bioimpedance measurement method, particularly a single-frequency bioimpedance measurement, preferably by a vector method, or a multi-frequency bioimpedance measurement, particularly with a body composition monitor (BCM), preferably by whole body bioimpeance spectroscopy, more preferably by segmental bioimpedance spectroscopy (BIS), even more preferably by normalized calf resistivity and most preferably by calf bioimpedance spectroscopy, f) the ratio between the total body water volume (TBW) and the extracellular water volume (ECV), and g) a blood volume measurement method, preferably by blood volume monitoring (BVM) and more preferably by determining the optical properties of blood in the intravascular compartment and most preferably by determining the densitometric properties of the intravascular compartment.

In one embodiment, the invention relates to a method for estimating a dry weight of a dialysis patient and/or a method of bringing an initially fluid-overloaded dialysis patient into his/her normal fluid status, wherein the second fluid status is determined by at least one of a blood volume measurement method, preferably by blood volume monitoring (BVM) and more preferably by determining the optical properties in the intravascular compartment and most preferably by determining the densitometric properties of the intravascular compartment and a segmental bioimpedance spectroscopy (BIS), preferably a calf bioimpedance spectroscopy (cBIS).

In one embodiment, the invention relates to a method for estimating a dry weight of a dialysis patient and/or a method of bringing an initially fluid-overloaded dialysis patient into his/her normal fluid status, further comprising the step of estimating a normal fluid status based on the first fluid status.

In one embodiment, the invention relates to a method for estimating a dry weight of a dialysis patient and/or a method of bringing an initially fluid-overloaded dialysis patient into his/her normal fluid status, wherein the first stage may end and/or the second stage may start, if the determined first fluid status falls below 2.5 to 0.25 L, preferably below 1.5 to 0.5 L and most preferably below 1 L of post-treatment session fluid overload compared to an estimated normal fluid status of the patient.

In one embodiment, the invention relates to a method for estimating a dry weight of a dialysis patient and/or a method of bringing an initially fluid-overloaded dialysis patient into his/her normal fluid status, wherein the normal fluid status is estimated by a whole body model or a method utilizing measurement of calf normalized resistivity.

In one embodiment, the invention relates to a method for estimating a dry weight of a dialysis patient and/or a method of bringing an initially fluid-overloaded dialysis patient into his/her normal fluid status, wherein the first stage may end and/or the second stage may start, if a blood volume monitoring shows that the relative blood volume (RBV) decreases during a treatment session.

In one embodiment, the invention relates to a method for estimating a dry weight of a dialysis patient and/or a method of bringing an initially fluid-overloaded dialysis patient into his/her normal fluid status, wherein the relative blood volume (RBV) decreases by more than 5%, preferably by more than 10%, more preferably by more than 15% and most preferably by more than 20% during a treatment session.

In one embodiment, the invention relates to a method for estimating a dry weight of a dialysis patient and/or a method of bringing an initially fluid-overloaded dialysis patient into his/her normal fluid status, wherein the first stage lasts approximately 1 to 6 months, preferably approximately 1 to 3 months and more preferably approximately 1 to 2 months.

In one embodiment, the invention relates to a method for estimating a dry weight of a dialysis patient and/or a method of bringing an initially fluid-overloaded dialysis patient into his/her normal fluid status, wherein the first fluid status is determined periodically, preferably every 1 to 6 weeks, more preferably every 2 to 4 weeks, even more preferably every 3 weeks, even more preferably every $10^{th}$ treatment (dialysis) session, even more preferably every $9^{th}$ treatment session, even more preferably every $8^{th}$ treatment session, even more preferably every $7^{th}$ treatment session, even more preferably every $6^{th}$ treatment session, even more preferably every $5^{th}$ treatment session, even more preferably every $4^{th}$ treatment session, even more preferably every $3^{th}$ treatment session, even more preferably every $2^{nd}$ treatment session and most preferably every treatment session.

In one embodiment, the invention relates to a method for estimating a dry weight of a dialysis patient and/or a method of bringing an initially fluid-overloaded dialysis patient into his/her normal fluid status, wherein the first fluid status and/or the second fluid status is measured during a treatment session.

In one embodiment, the invention relates to a method for estimating a dry weight of a dialysis patient and/or a method of bringing an initially fluid-overloaded dialysis patient into his/her normal fluid status, wherein the second fluid status is determined during every treatment session.

In one embodiment, the invention relates to a method for estimating a dry weight of a dialysis patient and/or a method of bringing an initially fluid-overloaded dialysis patient into his/her normal fluid status, wherein the estimated dry weight of a patient is determined by the evolution of the second fluid status during a treatment session.

In one embodiment, the invention relates to a method for estimating a dry weight of a dialysis patient and/or a method of bringing an initially fluid-overloaded dialysis patient into his/her normal fluid status, wherein the estimated dry weight of the patient is determined by analyzing the resistance curve and/or the normalized resistivity in the second stage.

In one embodiment, the invention relates to a method for estimating a dry weight of a dialysis patient and/or a method of bringing an initially fluid-overloaded dialysis patient into his/her normal fluid status, wherein the dry weight of the patient is considered as having been reached, if a flattening of the resistance curve of the patient recorded during a treatment session in the second stage is reached and/or the post-hemodialytic normalized resistivity of the patient is within the specific normal range of his/her comparison group comprising healthy individuals.

In one embodiment, the invention relates to a method for estimating a dry weight of a dialysis patient and/or a method of bringing an initially fluid-overloaded dialysis patient into his/her normal fluid status, wherein the resistance is measured by calf bioimpedance spectroscopy and/or the normalized resistivity of the patient is the normalized calf resistivity.

In one embodiment, the invention relates to a method for estimating a dry weight of a dialysis patient and/or a method of bringing an initially fluid-overloaded dialysis patient into his/her normal fluid status, wherein the first fluid status, the second fluid status, the estimated normal fluid status, the estimated dry weight or any other data gained throughout a dialysis session is transferred to a database, preferably via a data connection.

In one embodiment, the invention relates to a method for estimating a dry weight of a dialysis patient and/or a method of bringing an initially fluid-overloaded dialysis patient into his/her normal fluid status, wherein the database is operated at a central server.

In one embodiment, the invention relates to a method for estimating a dry weight of a dialysis patient and/or a method of bringing an initially fluid-overloaded dialysis patient into his/her normal fluid status, wherein the transferred data is processed such that statistics and/or conclusions for the treatment of the patient and/or a specific group of patients, in particular patients with comparable body parameters, may be derived.

In one embodiment, the invention relates to a method for estimating a dry weight of a dialysis patient and/or a method of bringing an initially fluid-overloaded dialysis patient into his/her normal fluid status, wherein the first fluid status, the second fluid status, the estimated normal fluid status, the estimated dry weight or any other data gained throughout the treatment session is used to determine the dosage of a medicament, preferably of EPO, antibiotics, and other parenterally-administered drugs.

In one embodiment, the invention relates to a medicament, preferably EPO, antibiotics, and other parenterally administered drugs, to be administered to a patient, wherein the dosage and/or the administration scheme of the medicament is determined according to a method for estimating a dry weight of a dialysis patient and/or a method of bringing an initially fluid-overloaded dialysis patient into his/her normal fluid status.

In one embodiment, the invention relates to an apparatus, particularly comprising a memory and a digital signal processor, configured to execute a method for estimating a dry weight of a dialysis patient and/or a method of bringing an initially fluid-overloaded dialysis patient into his/her normal fluid status.

In one embodiment, the invention relates to a computer program comprising instructions which, when being executed by a computer, cause the computer to execute a method for estimating a dry weight of a dialysis patient and/or a method of bringing an initially fluid-overloaded dialysis patient into his/her normal fluid status.

In one embodiment, the invention relates to a computer program product comprising instructions stored on a machine readable medium for the execution of a method for estimating a dry weight of a dialysis patient and/or a method of bringing an initially fluid-overloaded dialysis patient into his/her normal fluid status.

DETAILED DESCRIPTION

Figure 1A:
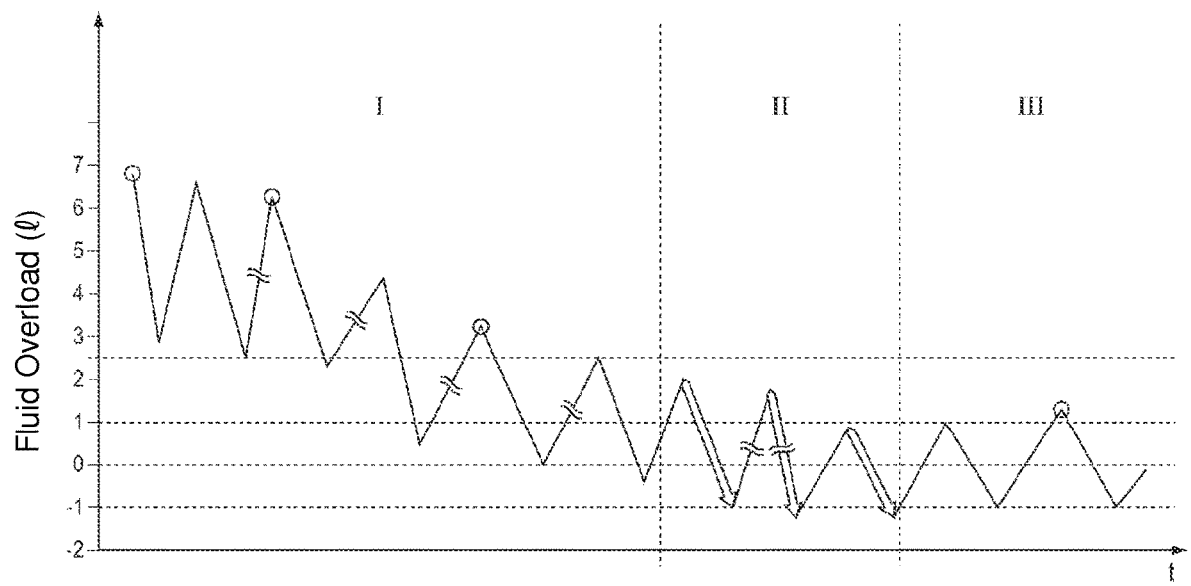
FIG. 1a is a diagram of the absolute fluid status versus time representing the evolution of the fluid status of a patient.

As discussed above, in various of its embodiments, the present disclosure relates to the problem of monitoring the fluid status in a patient. The patient will typically undergo hemodialysis, peritoneal dialysis or other forms of dialysis as a result of renal failure.

Nevertheless, the methods and apparatus disclosed herein can also be used to assess the fluid status and/or reduce the fluid overload of patients suffering from diseases other than renal failure, e.g., cardiac failure, liver failure, and/or chronic kidney disease which has not yet led to the need for dialysis treatment. For example, knowledge of dry weight can be of value with cardiac failure patients who are being treated with diuretics to reduce their fluid volume. As in dialysis, knowledge of the patient's dry weight is of clinical significance in deciding how much diuretic to prescribe.

In addition, the methods and apparatus can be used in connection with estimating the dry weight and/or reducing the fluid overload of normal subjects, e.g., individuals (athletes) participating in strenuous activity under high temperature and/or high humidity conditions. More generally, knowledge of a patient's dry weight may be beneficial in terms of controlling the intake of, for example, sodium in the patient's diet, e.g., the patient (either an ill subject or a normal subject) can monitor his or her fluid retention as a result of sodium intake by comparing his or her weight to an estimated or predicted dry weight determined in accordance with the present disclosure. Having information regarding dry weight may be of particular interest to fitness enthusiasts and other persons particularly concerned with their state of health.

The procedures and apparatus disclosed herein will typically be employed at various points in time so that an estimated dry weight will be current with changes in the individual's body composition, e.g., changes in the individual's fat and/or muscle content as a result of diet and/or exercise or the lack thereof.

In the sense of the present disclosure, a patient is any kind of individual, particularly a human or an animal, in a healthy or ill condition.

In the sense of the present disclosure, fluid overloaded means that the body of a patient comprises more fluid than in his/her normal fluid status corresponding to the normal fluid status weight, in particular a fluid excess.

In the sense of the present disclosure, a treatment session is defined as a periodically or irregularly recurring treatment of a patient.

In the sense of the present disclosure, during a treatment session is defined as the phase during which the patient undergoes a treatment.

In the sense of the present disclosure, fluid status is the level of fluid in a body composition of an individual.

In the sense of the present disclosure, dry weight is defined as the weight at which an individual is as close as possible to a normal fluid status or weight without experiencing symptoms indicative of fluid overload or deficit, i.e. the fluid status of the patient is such that the patient is above the hypovolemic symptomatic weight. In the sense of the present disclosure, normal fluid status weight is the gender-specific weight of a healthy individual.

In the sense of the present disclosure, reducing the fluid overload is the loss of body fluid having an influence on the fluid status of a patient.

In the sense of the present disclosure, the third stage is the maintenance stage, in which the patient is kept in a comparable small range of his/her fluid status. Maintaining the patient within said stage and the corresponding fluid status improves significantly the quality of life of the patient.

In the sense of the present disclosure, intradialytic is defined as during a dialysis session.

In the sense of the present disclosure, interdialytical is defined as between dialysis sessions.

In the sense of the present disclosure, the absolute fluid status difference is the difference between the current fluid status and the normal fluid status corresponding to the normal fluid status weight or dry weight.

In the sense of the present disclosure, resistance is a measure of the degree to which a patient's body opposes an electric current through it.

In the sense of the present disclosure, resistivity of a body segment, for example the calf, is the resistance of this segment divided by the distance between the recording electrodes used in the bioimpedance procedure and multiplied by an area representative of the average cross-sectional area of the segment, e.g., an actual average of cross-sectional areas of the patient's calf or an area of a representative cross-section of the patient's calf.

In the sense of the present disclosure, normalized resistivity is obtained by dividing the resistivity by the body mass index (BMI) of a patient, being the body weight in kilograms divided by the height in meters squared.

In the sense of the present disclosure, when a flattening of a resistance curve recorded during dialysis occurs (e.g., a flattening of a resistance curve continuously recorded during dialysis occurs), the slope of the resistance curve over time reaches a small absolute value or even approaches zero.

According the present disclosure, a dry weight of a dialysis patient is determined by the steps of determining a first fluid status of the patient between treatment sessions by either whole body bioimpedance spectroscopy using a physiological tissue model or a predictive calf resistivity model in a first stage (I), determining a second fluid status of the patient during treatment sessions using an intradialytic method (e.g., a continuous intradialytic method) in a second stage (II), and estimating the dry weight based on the second fluid status.

By embodiments of the disclosed methods, a maximally advantageous trade-off between the precision and cost-effectiveness of the diagnosis of the fluid status of a patient can be reached. In fact, in the first stage, less sensitive to an exact determination of the fluid status, an economical approach with a determination between treatment sessions is chosen, whereas in the second stage, where it is especially important to estimate an exact value of the dry weight, the more precise approach with determination during treatment sessions is chosen.

In stage I the patient does not have to undergo measurements requiring continuous measurement with electrodes on the patient.

For severely fluid-overloaded patients, it is advantageous to be monitored firstly with determinations between treatment sessions until a certain reduction of fluid overload with respect to the normal fluid status is achieved. From this point on, in certain embodiments, the patient can be adjusted to his/her dry weight using a monitoring with determinations during or after the treatment sessions.

To conclude, by the use of methods that combine a determination between treatment sessions with a determination of the fluid status of the patient during treatment sessions, the monitoring of the fluid overload of the patient can be arranged very effectively and conveniently for the patient, thus saving time and cost while ensuring a high quality of life to the patient.

According to the present disclosure an initially fluid-overloaded dialysis patient is brought into his/her normal fluid status by the steps of determining a first fluid status of the patient between treatment sessions in a first stage, reducing the fluid overload of the patient based on the first fluid status, determining a second fluid status of the patient during treatment sessions in a second stage and reducing the fluid overload of the patient based on the second fluid status.

By the method according to the present disclosure combining methods with determination of the fluid status between treatment sessions and during the treatment sessions, the fluid status of the patient can be guided smoothly towards a range of normal fluid status with the mass of a patient around the normal fluid status weight.

In fact, the body fluid is reduced in the first stage by gradually diminishing the weight, respectively the fluid overload, of a patient. Control of this reduction is performed between treatment sessions. Therefore, a first fluid status of the patient at a treatment session is compared to the change in the fluid status at a preceding treatment session. This is very time and cost effective, since a determination of the fluid status does not need to be performed at every treatment session.

Furthermore, this determination is very convenient for the patient, since it can be performed with a minimal interference. In some cases, a visual diagnosis of a physician might be enough to determine that the patient is still fluid overloaded.

The fluid overload of the patient is then reduced based on the determined first fluid status. This procedure is reiterated until a certain level of fluid overload is reached.

From this moment on, a second fluid status of the patient is determined during the treatment sessions. At this determination, the fluid status is not determined by comparing a measured second fluid status to a fluid status at a preceding treatment session. Instead, the continuously determined evolution during the treatment session serves as a criterion to determine the second fluid status. Alternatively, fluid status of the patient can be compared to the fluid status at the preceding treatment session by measuring calf resistivity. The fluid overload of the patient is then reduced based on this second fluid status.

FIG. 1a illustrates the development of the fluid status of a patient over time. According to the invention, this fluid status is divided in at least two stages (I, II). In the first stage (I), the patient has a severe fluid overload. In the second stage (II), the patient is in the range of normal fluid status. The normal fluid status is represented by the baseline in the diagram.

Thereby, the normal fluid status or weight gives an indication of a patient's optimum weight with respect to his/her fluid status with a range of approximately 1 to 2 kg. Dry weight, here shown as a fluid overload of zero litres, indicates a discrete fluid status, mostly comprised in the lower end of this range. The fluid status of the patient as described above is such that the patient should not experience hypovolemic symptoms, i.e. being above the hypovolemic symptomatic weight (HSW).

Figure 1B:
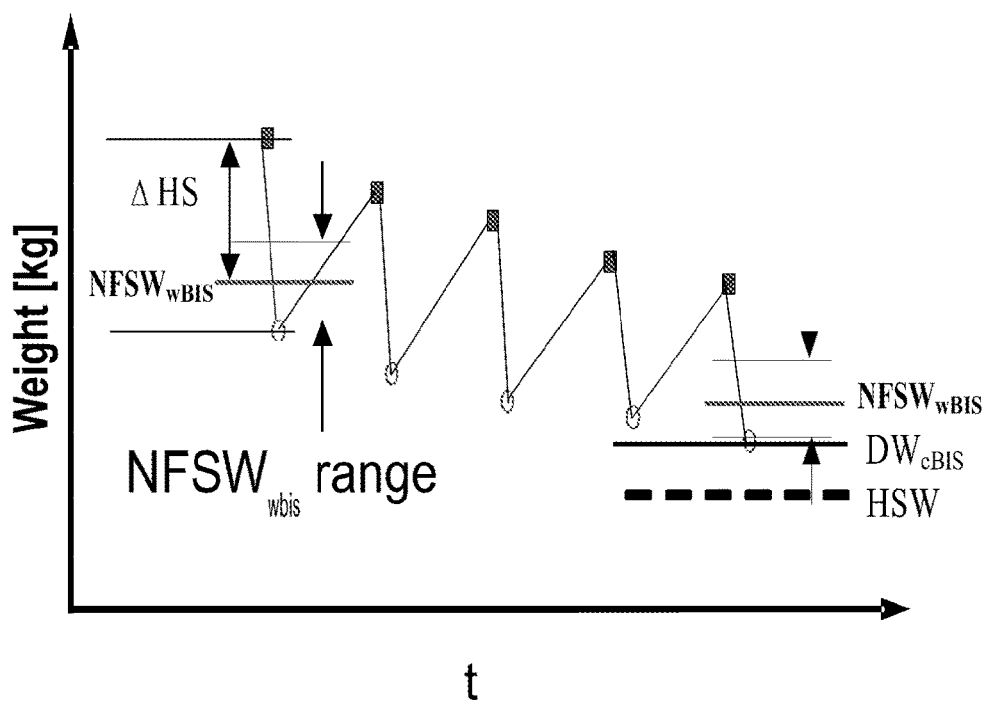
FIG. 1b illustrates schematically a typical arrangement of the dry weight as determined by calf bioimpedance spectroscopy ($DW_{cBIS}$) with respect to the hypovolemic symptoms weight (HSW) as well as the evolution of the normal fluid status weight as determined by whole body bioimpedance spectroscopy ($NFSW_{wBIS}$) over a series of dialysis sessions.

FIG. 1b illustrates schematically a typical arrangement of the dry weight as determined by calf bioimpedance spectroscopy ($DW_{cBIS}$) and the hypovolemic symptomatic weight (HSW) as well as the evolution of the normal fluid status weight as determined by whole body bioimpedance spectroscopy ($NFSW_{wBIS}$) or by calf resistivity in the normal range over a series of dialysis sessions. Usually, as will also be shown in the example below, the dry weight ($DW_{cBIS}$) is at the lower end of the normal fluid status weight ($NFSW_{wBIS}$) range estimated at any level of fluid overload of a patient.

The serrated curve represents the evolution of the fluid status. Each tooth corresponds to the period between two dialysis sessions. During the dialysis session, the fluid status drops. During the time period between two sessions, the amount of fluid in the patient's body rises gradually. Ideally, the fluid status does not reach the amount of fluid overload of the preceding pre-dialytic fluid status. Thus, over a longer period, the amount of fluid in the patient's body is reduced substantially as can be seen throughout the first and second stage (I, II) as defined by the present invention. Typically, at the beginning of the first stage (I) with the patient having a fluid overload of e.g. 7 L, the fluid status is reduced by approximately 3 to 4 L per dialysis session. At the end of the second stage (II) and/or during the third stage (III), the fluid status is reduced only by approximately 1.5 to 2.5 L per dialysis session. In this third stage, where the patient is supposed to be adjusted to his/her dry weight, no further permanent reduction of the fluid status is required. Instead, the patient shall be maintained "oscillating" between the dialysis sessions within and slightly around his/her normal fluid status or weight. Maintaining the patient within said stage (III) and the corresponding fluid status improves significantly the quality of life of the patient, since the patient does not have to undergo a process of interdialytic post- and/or predialytic fluid overload reduction which is in every case cumbersome for the patient.

The above reduction in the fluid overload of a patient is monitored by a method according to a first aspect of the present invention.

In one embodiment, at the start of applying the inventive method for estimating a dry weight of a dialysis patient, the current fluid status is determined. If the patient is severely fluid overloaded, meaning that the level of fluid overload is above 2.5 to 0.2 L, in one embodiment above 1.5 to 0.5 L and in one embodiment above 1 L of post-dialytic fluid overload compared to an estimated normal fluid status of the patient, the inventive method is applied. The current fluid status as well as the normal fluid status is thereby in one embodiment determined by estimating the normal fluid status weight with whole body bioimpedance spectroscopy (wBIS) and a whole body model ($NFSW_{wBIS}$) or by the normalized calf resistivity method. As will be explained below, estimating the absolute fluid status difference between the current fluid status and the normal fluid status can do this.

In another embodiment of the present invention, this determination of the current fluid status is performed with an intradialytic determination method, in one embodiment by monitoring the evolution of the fluid status using segmental bioimpedance spectroscopy, in particular on a patient's calf (CBIS), in one embodiment by monitoring the temporal evolution of the relative blood volume (RBV).

In the following, a first fluid status is determined interdialytically at certain dialysis sessions. In one preferred embodiment, the first fluid status is determined periodically, in one embodiment every 1 to 6 weeks, in one embodiment every 2 to 4 weeks and in one embodiment every 3 weeks.

In another embodiment, this determination is effectuated by a whole body bioimpedance spectroscopy (wBIS) or by calf normalized resistivity (CNR). If the fluid status did not change, exhibits an augmentation of the fluid overload or only a small reduction of the fluid overload compared to the preceding or initially determined fluid status, the dialysis therapy is continued and the inventive method remains within the first stage (I).

If an important reduction in the fluid status compared to the preceding or initial fluid status is assessed, the level of fluid overload is determined. In one preferred embodiment, this is effectuated by estimating the normal fluid status or weight ($NFSW_{wBIS}$) In another preferred embodiment, this is effectuated with an intradialytic determination method, in one embodiment the evolution of the fluid status using segmental bioimpedance spectroscopy, in particular on a patient's calf (CBIS).

If the determined level of fluid overload still exhibits severe fluid overload of the patient, the method is continued in the first stage (I).

If the determined level of fluid overloaded shows that the patient is still fluid overloaded but that the fluid status is within the range of the normal fluid status corresponding to the normal fluid status weight, the second stage (II) of the inventive method starts. According to one preferred embodiment, this condition is fulfilled if a determined fluid overload level falls below 2.5 to 0.25 L, in one embodiment below 1.5 to 0.5 L and in one embodiment below 1 L of fluid overload as compared to the normal fluid status or weight ($NFSW_{wBIS}$).

In yet another embodiment, the fluid status and/or the level of fluid overload is determined by the evolution of the blood volume of a patient during a dialysis session illustrated in FIG. 2.

The blood volume monitoring is effectuated during a dialysis session according to Rodriguez H. J. et al., "Assessment of dry weight by monitoring changes in blood volume using Crit-Line", Kidney Int. 2005 August, 68(2):854-61, which is incorporated by reference in its entirety. Plasma refilling rate is known to depend, amongst other factors, on the degree of fluid overload. Consequently, in general, a blood volume drop exhibits lower values at higher values of fluid overload at the same ultrafiltration rate. A decrease in blood volume at the end of a dialysis session is therefore expected when the range of the normal fluid status is reached. When monitoring the blood volume according to this embodiment, the second stage (II) starts, after an important drop over the course of a dialysis session has been observed.

Figure 2A:
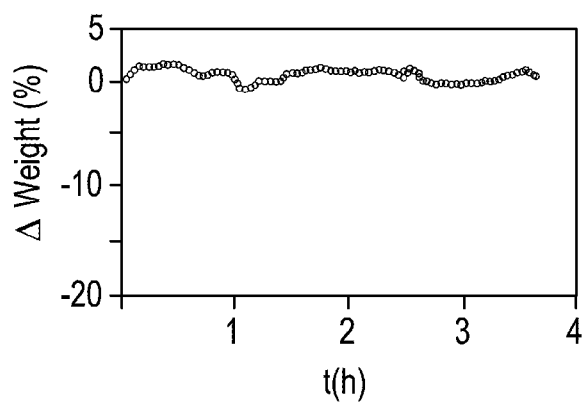
FIGS. 2a to c are diagrams of the relative blood volume (RBV) versus time representing the evolution of the blood volume of a patient at different fluid status of a patient.
Figure 2B:
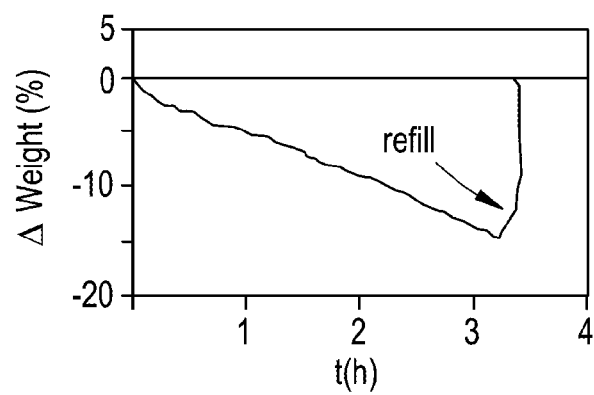
Figure 2C:
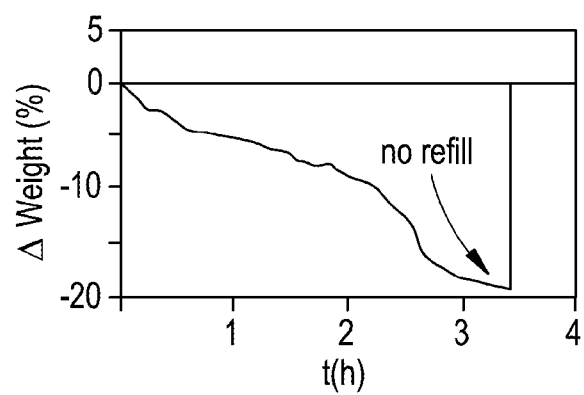

The diagrams of FIGS. 2a to c illustrate the evolution of the blood volume during a dialysis session wherein the ordinate (y-axis) denominates the difference in blood volume (BVΔ), expressed as Δwt. %, compared to the start of the session in percent and the abscissa (x-axis) denominates the lapsed time. FIG. 2a is the evolution of the relative blood volume (RBV) of a patient during a dialysis session when the patient is fluid overloaded at the beginning of the first stage (I) according to the present invention. FIG. 2b is the evolution of the relative blood volume (RBV) of a patient during a dialysis session when the patient is fluid overloaded at the end of the first stage (I)/at the beginning of the second stage (II) according to the present invention. FIG. 2c is the evolution of the relative blood volume (RBV) of a patient during a dialysis session when the patient has reached his/her normal fluid status and/or dry weight according to the present invention or is slightly hypovolemic.

An indication for the end of the first stage (I)/the beginning of the second stage (II) according to the present invention is that the relative blood volume (RBV) decreases by more than 5%, in one embodiment by more than 10%, in one embodiment by more than 15% and in one embodiment by more than 20% during a dialysis session.

According to this embodiment, the second stage (II) of the inventive method in one embodiment starts, when the evolution of the blood volume exhibits a slope corresponding to the curve in FIG. 2b or even to the curve in FIG. 2c.

However, the person skilled in the art understands that other conditions might apply to define the starting point of the second stage (II) of the inventive method. In further preferred embodiments, the fluid status is determined by a physical examination method, in one embodiment the observation of pedal edema, the measurement of blood pressure and/or the determination of jugular venous pressure (Agarwal R., Andersen M. J., Pratt J. H., "On the importance of pedal edema in hemodialysis patients", Clin. J. Am. Soc. Nephrol. 2008, 3:153-8; Thomson G. E., Waterhouse K., McDonald H. P. Jr., Friedman E. A., "Hemodialysis for chronic renal failure", Clinical observations, Arch. Intern. Med., 1967, 120:153-67; Charra B., Bergstrom J., Scribner B. H., "Blood pressure control in dialysis patients: importance of the lag phenomenon" Am. J. Kidney. Dis. 1998, 32:720-4; Borst J. G., Molhuysen J. A., "Exact determination of the central venous pressure by a simple clinical method", Lancet, 1952, 2:304-9), an imaging method, in one embodiment chest x-ray imaging and/or inferior vena caval diameter ultrasound imaging (Poggi A., Maggiore Q., "Cardiothoracic ratio as a guide to ultrafiltration therapy in dialyzed patients", Int. J. Artif. Organs, 1980, 3:332-7; Kouw P. M., Kooman J. P., Cheriex E. C., Olthof C. G., de Vries P. M., Leunissen K. M, "Assessment of postdialysis dry weight: a comparison of techniques", J. Am. Soc. Nephrol. 1993, 4:98-104; Cheriex E. C., Leunissen K. M., Janssen J. H., Mooy J. M., van Hooff J. P., "Echography of the inferior vena cava is a simple and reliable tool for estimation of 'dry weight' in haemodialysis patients", Nephrol. Dial. Transplant 1989; 4:563-8), biochemical markers, in one embodiment ΔNP, BNP, nT-pro BNP and/or cGMP (Yashiro M., Kamata T., Yamadori N., Tomita M., Muso E., "Evaluation of markers to estimate volume status in hemodialysis patients: atrial natriuretic peptide, inferior vena cava diameter, blood volume changes and filtration coefficients of microvasculature", Ther. Apher. Dial. 2007; 11:131-7; Chazot C., Vo-Van C., Zaoui E., "Fluid overload correction and cardiac history influence brain natriuretic peptide evolution in incident haemodialysis patients. Nephrol Dial Transplant", Lee J. A., Kim D. H., Yoo S. J., Oh D. J., Yu S. H., Kang E. T., "Association between serum n-terminal pro-brain natriuretic peptide concentration and left ventricular dysfunction and extracellular water in continuous ambulatory peritoneal dialysis patients", Prtit. Dial. Int. 2006, 26:360-5; Rosner M. H., "Measuring risk in end-stage renal disease: is N-terminal pro brain natriuretic peptide a useful marker?", Kidney. Int. 2007, 71:481-3; Osajima A., Okazaki M., Kato H., "Clinical significance of natriuretic peptides and cyclic GMP in hemodialysis patients with coronary artery disease", Am. J. Nephrol. 2001, 21:112-9; Kuhn C., Kuhn A., Rykow K., Osten B., "Extravascular lung water index: a new method to determine dry weight in chronic hemodialysis patients", Hemodial. Int. 2006, 10:68-72), a thermal dilution determination method, in one embodiment extravascular lung index determination (Kuhn C., Kuhn A., Rykow K., Osten B., "Extravascular lung water index: a new method to determine dry weight in chronic hemodialysis patients", Hemodial. Int., 2006, 10:68-72), a bioimpedance measurement method, particularly a single-frequency bioimpedance measurement, in one embodiment by a vector method, or a multi-frequency bioimpedance measurement, particularly with a BCM, in one embodiment by whole body bioimpedance spectroscopy, in one embodiment by segmental bioimpedance spectroscopy (BIS) or calf normalized resistivity Zhu F, Kotanko P, Levin W L., Estimation of normal hydration in dialysis patients using whole body and calf bioimpedance analysis, Physiol. Meas., 2011 32:887-902 R and in one embodiment by calf bioimpedance spectroscopy (Piccoli A., Rossi B., Pillon L., Bucciante G., "A new method for monitoring body fluid variation by bioimpedance analysis: the RXc graph", Kidney. Int. 1994, 46:534-9; Moissl U. M., Wabel P., Chamney P. W., "Body fluid volume determination via body composition spectroscopy in health and disease", Physiol. Meas., 2006 27:921-33; Chamney P. W., Kramer M., Rode C., Kleinekofort W., Wizemann V., "A new technique for establishing dry weight in hemodialysis patients via whole body bioimpedance", Kidney Int., 2002, 61:2250-8; Zhu F., Kotanko P., Handelman G. J., "Estimation of normal hydration in dialysis patients using whole body and calf bioimpedance analysis", Physiol. Meas. 2011, 32:887-902; Zhu F., Kuhlmann M. K., Kotanko P., Seibert E., Leonard E. F., Levin N. W., "A method for the estimation of hydration state during hemodialysis using a calf bioimpedance technique", Physiol. Meas. 2008, 29:503-16; Lopot F., Nejedly B., Novotna H., Mackova M., Sulkova S., "Age-related extracellular to total body water volume ratio (Ecv/TBW)—can it be used for "dry weight" determination in dialysis patients? Application of multifrequency bioimpedance measurement", Int. J. Artif. Organs, 2002, 25:762-9), the ratio between the total body water volume (TBW) and the extracellular water volume (ECV), and a blood volume measurement method, in one embodiment by blood volume monitoring (BVM) and in one embodiment by determining the optical properties in the extracellular compartment (Lopot F., Nyiomnaitham V., Svarova, Polakovic V., Svara F., Sulkova S., "Continuous blood volume monitoring and "dry weight" assessment", J. Ren. Care 2007, 33:52-8); Booth J., Pinney J., Davenport A., "Do changes in relative blood volume monitoring correlate to hemodialysis-associated hypotension?", Nephron. Clin. Pract., 117: 179-83; Sinha A. D., Light R. P., Agarwal R., "Relative plasma volume monitoring during hemodialysis AIDS the assessment of dry weight", Hypertension, 55:305-11), the disclosures of which are entirely incorporated by reference.

In the following a second fluid status is determined with an intradialytic measurement during certain dialysis sessions, in one embodiment during every dialysis session.

In one preferred embodiment, the intradialytic measurement is performed by segmental bioimpedance spectroscopy, in one embodiment by calf bioimpedance spectroscopy (cBIS).

In this preferred embodiment, the evolution of the relative resistance and/or the normalized resistivity CNR (ρBMI) during the course of a dialysis session is evaluated continuously or intermittently. Corresponding diagrams are illustrated in FIGS. 3 and 4.

The slope of change in the relative resistance represents the removal of excess fluid volume in the considered segment of a body, here the calf. A flattening of the relative resistance curve means that the fluid exchange between intravascular and interstitial compartments has reached an equilibrium state. Therefore, the normal fluid status corresponding to the dry weight of the patient is reached, if the curve of the relative resistance becomes flat. This means, that the slope of the resistance curve over time reaches a small absolute value or even becomes zero.

Figure 3:
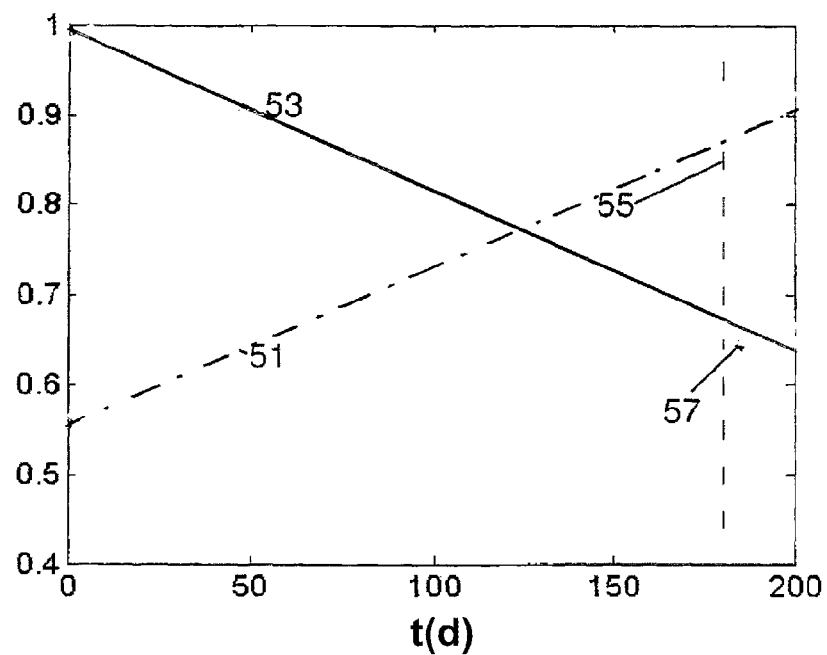
FIG. 3 is a diagram of the relative resistance R (t=0)/R (t) and the calf normalized resistivity (CNR; also referred to as $\rho N$ in this document) versus time representing the evolution of these parameters for a fluid-overloaded patient.

FIG. 3 illustrates an evolution of the relative resistance represented by the ratio R (t=0)/R (t) (continuous line) and of the normalized resistivity (dotted line) between the start of a dialysis session (at 0 minutes) and the end of a session (after 200 minutes). From the curve of the relative resistance, it becomes clear that the relative resistance decreases linearly. Therefore, dry weight has not yet been reached.

Figure 4:
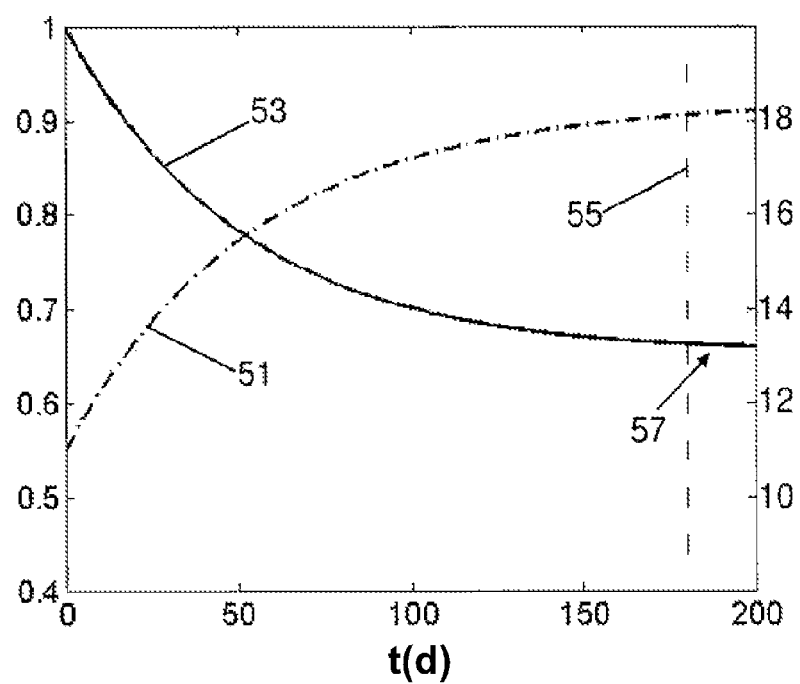
FIG. 4 is a diagram of the relative resistance R (t=0)/R (t) and the normalized resistivity $\rho N$ versus time representing the evolution of these parameters for a patient when dry weight has been reached.

FIG. 4 illustrates another evolution of the relative resistance (R (t=0)/R (t)) and of the normalized resistivity CNR. One can see that the relative resistance flattens at the end of the dialysis session. Furthermore, CNR lies at 18, corresponding to the gender specific range of dry weight of this specific patient. Therefore, dry weight has been reached.

An alternative criterion to determine intradialytically if the dry weight is reached is the evolution of the relative blood volume as described above in relation to the end of the first stage (1)/the beginning of the second stage (II). Dry weight is then reached when the curve over time exhibits a form equivalent to FIG. 2c.

An additional criterion to confirm that the normal fluid status corresponding to the dry weight of the patient is reached, consists in one embodiment in determining whether the normalized resistivity is in the gender specific range of normal fluid status of the patient. It is understood by the person skilled in the art, that this is only an optional criterion and not necessarily needed to determine the dry weight of a patient.

In one embodiment according to the inventive method, the intradialytic measurement is performed during every dialysis session as indicated by the flashes on the fluid status curve of FIG. 1 in the second stage (II). By the intradialytic measurement, the fluid status of the patient can be determined very accurately and monitored steadily. This is especially important, since the dry weight is only slightly above the hypovolemia symptomatic weight (HSW) where the patient starts suffering form hypovolemic symptoms.

The intradialytic measurement and thus the second stage (II) of the inventive method is stopped once the patient reaches a stable condition of fluid status in the range of the normal fluid status or weight. In one embodiment, the fluid status of the patient then oscillates around the normal fluid status as indicated in the third stage (III) of FIG. 1.

In this third stage (III), the fluid status of the patient is determined interdialytically, as in the first stage (I). The periodicity of the determinations of the fluid status can be less frequent, since the patient is adjusted to the correct fluid status, i.e. to a fluid status oscillating around the normal fluid status. The third stage (III) can be designated as a fluid status maintenance phase. The patient should be maintained at the optimal fluid status after having been adjusted in his/her fluid status. The aim in the third stage (III) of diagnosis is to provide a relatively precise estimation of the fluid status of the patient while keeping the inconvenience of the determination by measurement as low as possible. Therefore, as long as a patient is oscillating in his/her fluid status around his/her normal fluid status or weight, an interdialytic determination with a low frequency of determinations between dialysis sessions can be made.

If a patient feels uncomfortable or the fluid overload and/or the weight of a patient start to rise again, the inventive method may be applied again, starting from the second stage (II) to newly determine a changed dry weight of a patient and to adjust the patient to this new dry weight. Such change of weight might be induced by a change of the body weight of the patient, e.g. due to more or less body fat or muscle, or by some other change of the body composition of the patient.

In a further method of bringing an initially fluid-overloaded dialysis patient into a normal fluid status, the same or equivalent steps as explained above are applied.

The difference between this method and the foregoing consists in the fact that additionally to determining a first fluid status in a first stage (I) and a second fluid status in a second stage (II), the patient's fluid overload is also reduced based on the first or second fluid status during each of the stages, respectively.

The amount of fluid which is removed from the body during a dialysis session is either determined based on the information of the relative weight loss with respect to a previous session, the estimated normal fluid status and the absolute fluid status difference, respectively, or the estimated dry weight of a patient.

The absolute fluid status difference is the difference between the determined fluid (overloaded) status and the normal fluid status. Both, the fluid status and the normal fluid status can be referred to in liters or in kilogram. As it will be shown in the example below, a 1 kg decrease in body weight during a dialysis session corresponds roughly to 1 L reduction in body fluid volume.

Whereas the normal fluid status gives an indication of a patient's optimum weight with respect to his/her fluid status with a range of approximately 1 to 2 kg around this weight, the dry weight indicates a discrete fluid status comprised in this range. As already explained above, the dry weight is thereby the weight at which an individual is as close as possible to a normal fluid status without experiencing symptoms indicative of fluid overload or deficit, i.e. the fluid status of the patient is such that the patient is above the hypovolemic symptomatic weight (HSW) as illustrated in FIG. 1b. Usually, the dry weight is below a determined value of a normal fluid status or weight (NFSW$_{wBIS}$) but within the range of normal fluid status.

Again, the different stages (I,II,III) of the inventive method define different phases of fluid status, where different techniques of determination of the fluid status giving the basis for fluid reduction has advantages with respect to economical aspects, with respect to the comfort of the patient and/or with respect to the needed precision of determination.

During the first stage (I), where the fluid status is determined interdialytically, the patient's fluid overload is in one embodiment reduced at most to a level corresponding to a loss of 0.5 kg, in one embodiment 0.3 kg, in one embodiment 0.2 kg and in one embodiment 0.1 kg of body weight during each dialysis session in the first stage (I). This is important in order not to induce intradialytic symptoms of hypovolemia. In other preferred embodiments, this limit might also be set to the fluid overload reduction in the second and/or third stage (II; III) of the inventive method. This limited reduction ensures that, even though the dry weight of the patient cannot be determined exactly, the patient does not suffer hypovolemic symptoms during a session.

During the second stage (II), the dry weight of the patient can be determined exactly by intradialytic determination. This serves to correctly adjust the patient to his/her normal fluid status weight.

In the third stage (III), the maintenance phase, the determination method of the fluid status is again interdialytic, such that the fluid status is under control without causing disproportional costs and/or discomfort to the patient.

The bioimpedance methods used for the determination of the fluid status and/or the estimation of the dry weight, the ratio of wECV/wTBW, the whole body model (WBM), the calf normalized resistivity (CNR) method, and the continuous cBIS are presented in the following with respect to FIGS. 5 to 9:

a) Whole Body Bioimpedance Spectroscopy (wBIS)

Figure 5:
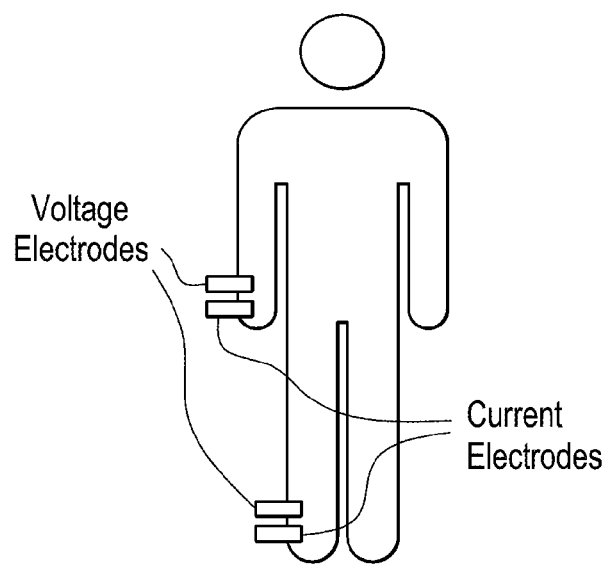
FIG. 5 is a schematic drawing illustrating a representative placement of electrodes on an individual's body for performance of a whole body bioimpedance spectroscopy.

Bioimpedance is a non-invasive technique. In a typical application, current is injected into the subject via a pair of stimulating electrodes placed on the wrist and ankle of a patient, as shown in FIG. 5. An additional pair of recording electrodes monitors the resulting potential difference. The degree of conduction of current through the intracellular compartment is frequency dependent due to the presence of the cell membrane that exhibits similar electrical properties to those of an electrical capacitor. Since the potential difference developed across the tissue also undergoes a phase shift with respect to the applied current (due to the cell membrane), the overall measurement is known as the "impedance" signifying the dependence on frequency. An application of low frequency alternating current causes conduction almost exclusively through the extracellular spaces of the tissues. At low frequency the cell membrane behaves as an insulator inhibiting the passage of current. In the high frequency range the cell membranes conduct and current passes through both the intracellular and extracellular spaces.

By analysis of the impedance and phase shift at different frequencies, the resistance of the extracellular water volume (ECV; $R_E$) and intracellular water volume (ICV; $R_I$) of the body tissue may be derived. The values of both $R_E$ and $R_I$ depend on the volume of fluid in the respective tissue compartments. By combining anthropometric measurements of body segments and tissue resistivity constants determined from dilution studies, ECV and ICV may be calculated.

b) Whole Body Model (WBM) for Estimating the Fluid Status

As explicated above, the amount of severe fluid overload is underestimated with wBIS.

To overcome these limitations of the wBIS method, an advanced whole body composition model (WBM) based on the assessment of wECV, wICV, wTBW and fat mass has been developed recently as described in Chamney P. W., Wabel P., Moissl U. M. et al., Am. J. Clin. Nutr., 2007, January, 85(1):80-9, the disclosure of which is entirely incorporated by reference. The WBM incorporates an assessment of the fluid components of the body compartments and calculates the absolute fluid status difference (ΔHS) between the current fluid status and the normal fluid status or normal fluid status weight (NFSW$_{wBIS}$) by employing pre-dialytic measurements of wECV, wICV and body weight (BW). This model is based in part on the concept of constant fluid status of normohydrated lean and adipose tissue. Clinical reports have shown this to be a useful method for fluid assessment.

In the below example, this model was applied using wECV and wICV measured with the Hydra 4200 and recalculated according to Chamney P. W., Wabel P., Moissl U. M. et al., Am. J. Clin. Nutr., 2007, January, 85(1):80-9, PCT patent application WO2006/002656 A1 and/or PCT patent application WO2006/002685, the disclosures of which are entirely incorporated by reference. It allows the patient specific prediction of the normal fluid status and the normal fluid status weight—the weight the patient would have with a working kidney.

Predicted weight at normal fluid status (NFSW$_{wBIS}$) by WBM can be described by $$NFSW_{wBIS} = \text{pre-dialytic weight} - \Delta HS \text{ [kg]} \quad (1)$$

with the absolute difference in fluid status (ΔHS) or the mass of excess fluid or excess fluid volume being $$\Delta HS = [ECW_{WB} - H_{ECE\_NH\_AT} X M_{WB} + kX(ICW_{WB} - H_{ICW\_NH\_AT} X M_{WB})]/[H_{ExF} - (H_{ECW\_NH\_AT} + kXH_{ICW\_NH\_AT})] \text{ [kg]} \quad (2)$$

wherein $$H_{ECW\_NH\_AT} = M_{ECW\_NH\_AT}/M_{NH\_AT} \quad (3)$$

$$H_{ICW\_NH\_AT} = M_{ICW\_NH\_AT}/M_{NH\_AT} \quad (4)$$

$$H_{ExF} = M_{ExW}/M_{ExF} \quad (5)$$

$$k = (H_{ECW\_NH\_AT} - H_{ECW\_NH\_LT})/(H_{ICW\_NB\_LT} - H_{ICW\_N H\_AT}) \quad (5)$$

with NH designating the normal fluid status, ΔT being the adipose tissue, and LT being lean tissue c) Calf Bioimpedance Measurements for Determining Dry Weight (DW$_{cBIS}$)

Calf bioimpedance spectroscopy (cBIS) for determination of actual dry weight, termed DW$_{cBIS}$, uniquely does not require comparison of fluid volumes with a normal population.

The purpose of the measurement is to obtain information concerning the calf's extracellular water volume (cECV).

d) Resistivity Method

The dry weight estimation is based on the performance of a bioimpedance measurement on the individual's calf. The calf was chosen because the calf has been shown to be more hydrated because of gravity than other body segments such as the arm and trunk.

In practice, it has been found that resistance values obtained for a stimulating frequency of 5 kHz results in highly accurate estimations of dry weight ($DW_{cBIS}$), it being understood that other frequencies can be used and that instead of a resistance value, a value for the magnitude of the impedance (|Z|) at 5 kHz or at another frequency can be used. In a similar manner, combinations of resistance values and/or impedance values at a plurality of frequencies can be used, e.g., an average R value, an average |Z| value, or an average over Rvalues for a plurality of frequencies (e.g., 1, 5 and 10 kHz) can be used.

Figure 6:
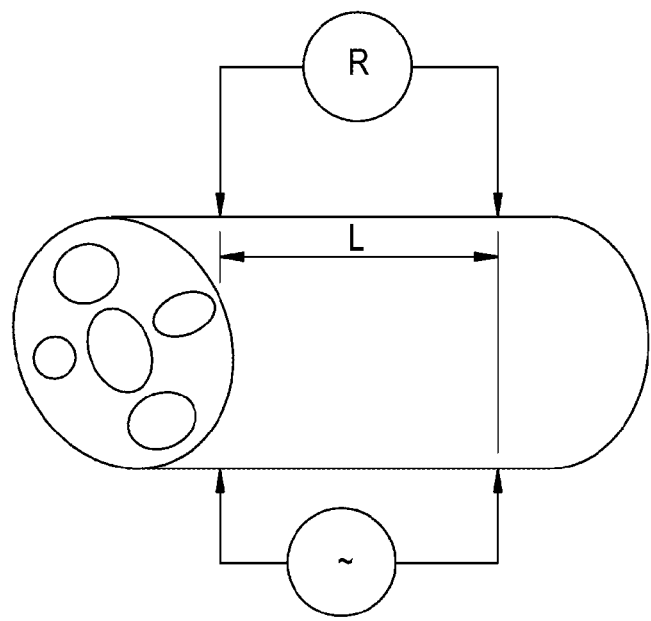
FIG. 6 is a schematic drawing illustrating the elements of a bioimpedance measurement.

FIG. 6 is a schematic diagram illustrating the basic elements involved in the performance of a bioimpedance measurement on an individual's calf. As shown, the bioimpedance system includes a stimulating system which applies an $\Delta C$ current at two spaced apart locations on the surface of a patient's calf and a recording system which detects the resulting AC voltage difference at two spaced apart locations, which are in one embodiment inboard of the stimulating locations. The AC voltage difference is then used to calculate a bioimpedance value or, in some cases, simply a resistance (R) value.

The procedure is in one embodiment performed at one frequency, e.g., 5 kHz, or in one embodiment at a plurality of frequencies. The technique is referred to as calf bioimpedance spectroscopy (cBIS).

Figure 7:
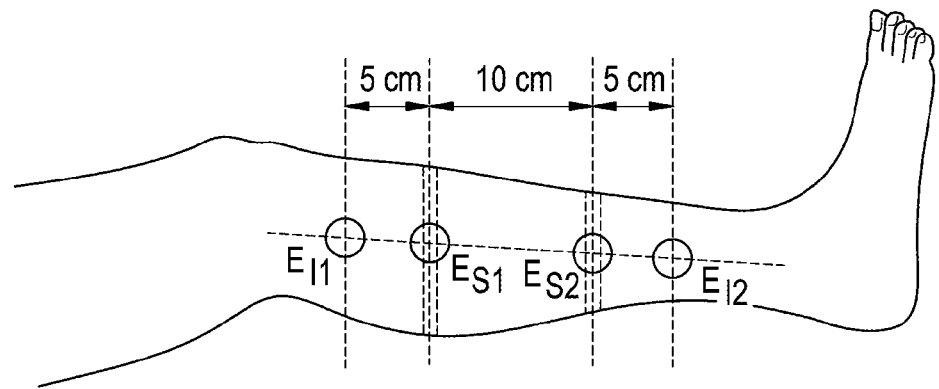
FIG. 7 is a schematic drawing illustrating a representative placement of electrodes on an individual's calf for performance of bioimpedance spectroscopy for the calf.

FIG. 7 shows representative locations of the stimulating electrodes ($E_{11}$ and $E_{12}$) and recording electrodes ($E_{S1}$ and $E_{S2}$) used in the bioimpedance procedure on a patient's calf. As illustrated in this figure, a convenient location for $E_{S1}$ is at the calf's maximal circumference ($C_1$), with $E_{S2}$ being placed 10 cm distal to the maximal circumference and $E_{S1}$, respectively. In the example below, the two stimulating electrodes $E_{11}$ and $E_{12}$ were placed, one 5 cm proximal of $E_{S1}/C_1$, the other 5 cm distal of $E_{S2}/C_2$.

$DW_{cBIS}$ is defined as the weight at which a flattening of the resistance curve (R (t=0)/R (t)) recorded during dialysis occurs. cBIS has been validated clinically by reducing post-dialytic weight below $DW_{cBIS}$ with this intervention resulting in hypotension and other symptoms of hypovolemia, i.e. $DW_{cBIS}$ is the lowest body weight of a patient over the hypovolemia symptomatic weight (HS W).

Figure 9:
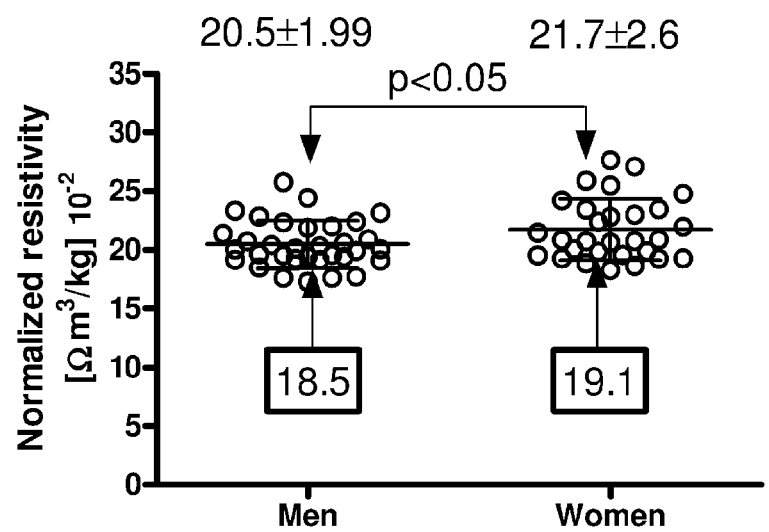
FIG. 9 is a plot of calf normalized resistivity (CNR) values for healthy subjects. The minimal acceptable normal hydration line ($18.5*10^{-1}$ [$\Omega m^3/kg$] in men and $19.1*10^{-1}$ [$\Omega m^3/kg$] in women) is defined as the mean of CNR in healthy subjects minus one standard deviation.

In addition to the flattening of the resistance curve (R (t=0)/R (t)), in order to confirm the presence of $DW_{cBIS}$, it is in one embodiment determined whether the calf normalized resistivity ($\rho N$) of a patient is within the respective gender-specific post-dialytic normal range. FIG. 9 shows calf normalized resistivity values determined for healthy men and women.

The calf normalized resistivity ($\rho N$) is calculated according to Zhu et al., "A method for the estimation of hydration state during hemodialysis using a calf bioimpedance technique", Physiol. Meas., 2008: S503-S516, which is incorporated by reference in its entirety. The resistivity value is determined from the equation:

$$\rho = R \cdot A/L \; [\Omega \sim m] \quad (7)$$

where A is the cross-sectional area calculated by, for example, an average of two circumferences:

$$A = (C_1 + C_2)^2/(16 \cdot \pi) \; [m^2] \quad (8)$$

where, as illustrated in FIG. 6, L is the spacing between the recording electrodes used in the bioimpedance procedure (here L=0.1 m), A is the area of a representative cross-section of the individual's calf, C in meters is the circumference value for the individual's calf obtained from one or more circumference measurements performed on the calf, and R is the resistance value for the calf obtained from the bioimpedance procedure.

The $\rho$ value obtained from Equation (7) is next normalized by being divided by the individual's body mass index (BMI=body weight [kg]/(body height [m])$^2$), i.e., the normalized resistivity $\rho N$ (also referred to as "nRho") is given by:

$$\rho N = \rho/BMI \; [\Omega \cdot m^3/kg] \quad (9)$$

Figure 8:
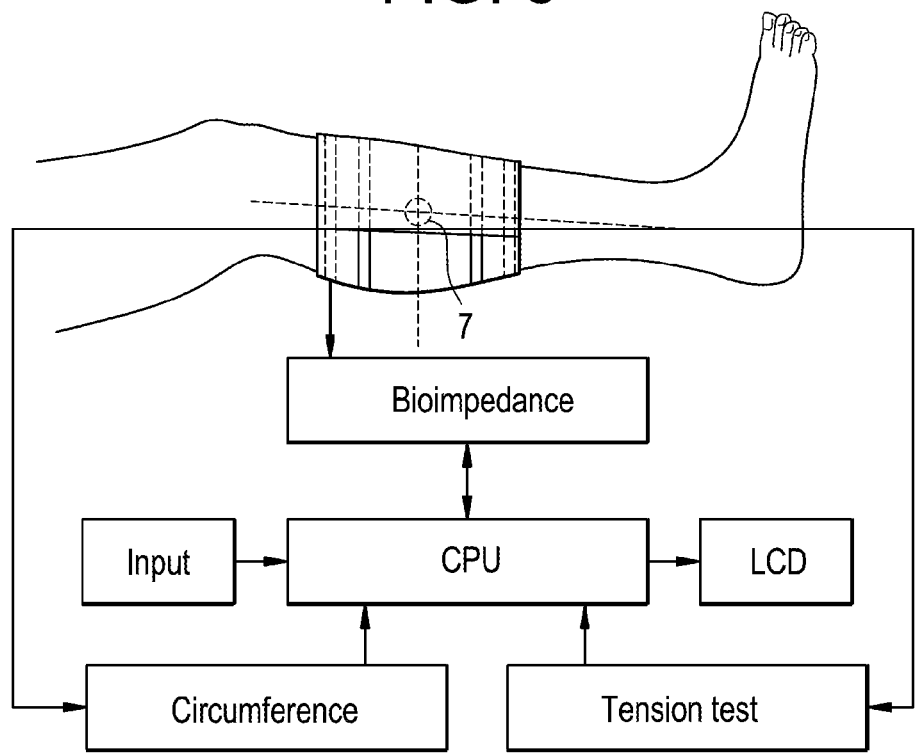
FIG. 8 is a schematic drawing illustrating representative hardware and software components for practicing calf bioimpedance spectroscopy.

FIG. 8 illustrates a representative processing system for receiving and analyzing bioimpedance and other data for the individual whose dry weight is to be estimated. Even though the system is represented for cBIS only, it shall be understood that the same system with other electrodes can be applied to wBIS. As shown in this figure, the system can include a central processing unit (CPU), which receives measured data from bioimpedance system, as well as other types of input from the input module, e.g., input relating to the individual's sex, weight, height, etc., which can be keyed in or electronically provided. The system can also include a display module, in one embodiment a display module employing a liquid crystal display (LCD), for providing information to the user as well as a keyboard (not shown) connected to the input module with which the user can provide information to the system.

As illustrated in FIG. 8, the bioimpedance system in one embodiment employs a pressure cuff 7 that carries stimulating electrodes (e.g., $E_{11}$ and $E_{12}$ of FIG. 7) and recording electrodes (e.g., $E_{S1}$ and $E_{S2}$ of FIG. 7). The electrodes can be disposable or reusable as desired. The pressure cuff can be employed as part of the process of determining a value for the circumference of the patient's calf, e.g., through the use of the circumference module of FIG. 8. For example, using a tension sensor, a tension test can be performed by the tension testing module of FIG. 8 to determine that the individual's calf has been compressed to a desired extent before the circumference is determined. The circumference can be determining by various methods such as by an electrical resistance technique of the type disclosed in PCT Patent Publication No. WO 2005/027717, the contents of which in their entirety are incorporated by reference. The circumference can, for example, be measured at the locations of the recording electrodes (or at one or more other convenient locations) and, if multiple measurements are made, averaged to provide a mean value. Rather than using a pressure cuff, the circumference can be determined manually using a flexible tape measure. Again, one measurement can be used, or multiple measurements can be made and then averaged. Other techniques for determining the circumference of the individual's calf can be used as desired. However determined, a circumference value is ultimately provided to a CPU and then used in determining a resistivity value for the individual's calf.

According to the invention, all of the necessary elements to effectuate the inventive method may be implemented in one apparatus. This involves the necessary hardware to perform whole body bioimpedance spectroscopy, calf bioimpedance spectroscopy and/or relative blood volume monitoring, to control the needed measurements and to calculate the above specified parameters based on the measurements. In particular, such an apparatus may comprise a memory and a digital signal processor, a first determination unit configured to determine a first fluid status of the patient between treatment sessions in a first stage (I), a first reduction unit to reduce the fluid overload of the patient based on the first fluid status, a second determination unit to determine a second fluid status of the patient during treatment sessions in a second stage (II) and/or a second reduction unit to reduce the fluid overload of the patient based on the second fluid status. In a further embodiment the apparatus comprises a third determination and/or a third reduction unit. These units are each configured to perform necessary actions in order to implement the inventive methods. In a further embodiment, such an apparatus is further adapted to control the fluid status of a patient automatically in order to reduce the fluid overload of a patient.

Example

The experimental procedure of the example was as follows. The experimental procedure was approved by the Institutional Review Board of Beth Israel Medical Center, New York. Written informed consent was obtained from all participants.

Method

Twenty-one fluid-overloaded maintenance hemodialysis patients (11 male/10 female, age 58±13 years) from Beth Israel Medical Center and Renal Research Institute dialysis facility were studied. By using continuous cBIS to determine $DW_{cBIS}$, the fluid status was evaluated at the beginning of the study in all patients: if $DW_{cBIS}$ criteria were not met at the end of the first session in a first stage (I), dialytic post-hemodialytic weights were reduced by 0.2 to 0.3 kg in each subsequent session. Once patients had reached $DW_{cBIS}$, patients were defined to be in the target area of the second stage (II).

Monitoring of the reduction of the patients' fluid status was effectuated by continuous cBIS at every subsequent session. In parallel, the ratio of ECV/TBW determined by wBIS was monitored. From this, also the normal fluid status was determined using the above specified physiological tissue model, namely the whole body model (WBM). Patients who reached dry weight as determined by continuous cBIS ($DW_{cBIS}$) comprised the $DW_{cBIS}$-patient group, the remainder the non-$DW_{cBIS}$-patient group.

In the present example, pre- and post-hemodialytic whole body bioimpedance spectroscopy (wBIS) was performed while patients were in a supine position at each dialysis session, using the Hydra 4200 (Xitron Technologies Inc., San Diego, Calif.). wBIS measurements were performed pre-hemodialytic over a range of 50 frequencies (5 kHz to 1000 kHz) via electrodes placed on the wrist and ankle to measure the whole body extracellular water volume (wECV), the whole body intracellular water volume (wICV) and to calculate the total body water volume (TBW). The wECV and wICV were calculated using equations modified by Moissl U. M., Wabel P., Chamney P. W., et al., "Body fluid volume determination via body composition spectroscopy in health and disease", Physiol. Meas., 2006, 27:921-933, incorporated by reference in its entirety. wBIS measurements were also performed some minutes after the end of the dialysis session. The ratios of wECV/TBW and of wECV/wICV were used to indicate fluid status at the different stages of the study.

Intradialytic extracellular calf resistance (R) was measured continuously by cBIS using a modified Hydra device 4200. The instantaneous ratio R (t=0)/R (t) was determined from these measurements (R (t=0) is R at the start of the dialysis session; R (t) is R at time t and reflects the intradialytic change in calf ECV). A resistance at 5 kHz has been chosen as the bioimpedance value.

Systolic (SBP) and diastolic blood pressures (DBP) were measured pre- and post-hemodialytic (using a Blood Pressure Module, Fresenius 2008K Dialysis Machine). Ultrafiltration rate (UFR) and ultrafiltration volume (UFV) were recorded throughout each session.

Statistical Analysis

Statistical analyses were performed using SPSS software version 15.0 (SPSS Inc., Chicago, Ill., USA) and the GraphPad Prism 5 (GraphPad Software Inc., San Diego, Calif.). Data are reported as mean±standard deviation (SD). In order to compare volume and fluid status parameters at different fluid status before reaching $DW_{cBIS}$, the post-hemodialytic body weights for each patient were categorized into three subgroups by dividing the difference in post-hemodialytic weight between baseline and $DW_{cBIS}$ by three to represent three different phases of fluid status (corresponding to the first and second stage (I, II) according to the invention) before reaching $DW_{cBIS}$. The first stage (I) represents the baseline measurement that indicates a state of fluid overload for all patients. Paired t-tests were used for comparison between the first stage (I) and the end of study. The relationships between $NFSW_{WBIS}$ and $DW_{cBIS}$ were analyzed by simple linear correlation and Bland-Altman analysis. In order to assess the clinical significance of the differences in fluid status as estimated by cBIS and WBM, mean systolic (SBP) and diastolic (DBP) blood pressure were compared at different fluid status. P values less than 0.05 were considered statistically significant. It was assumed that a 1 kg decrease in body weight during a hemodialysis session represented a 1 L reduction in body fluid volume. Body composition was assumed to stay constant over the course of the study.

Results

At the end of the experiment, two groups of patients had to be differentiated: one group had reached $DW_{cBIS}$ ($DW_{cBIS}$-patients); the other group did not (non-$DW_{cBIS}$-patients). Nine (43%) out of 21 patients reached $DW_{cBIS}$ defined by cBIS and 12 patients (57%) did not reach $DW_{cBIS}$. $DW_{cBIS}$ was reached within 50±30 days within the $DW_{cBIS}$-patients group. For the non-$DW_{cBIS}$-patients, the study was stopped after 45±24 days.

The intradialytic change in wECV showed a good agreement with the intradialytic change in bodyweight (−0.109 kg±0.77 kg in stage 1 and −0.035 kg+0.77 kg at the end of the experiment). Thus 1 kg decrease in body weight during a hemodialysis session was confirmed to correspond to 1 L reduction in body fluid volume.

In the group of $DW_{cBIS}$-patients, a flattening of the R (t=0)/R (t) curve occurred and post hemodialysis ρN increased into the gender-specific normal range (ρN at baseline 18.2±3.0*$10^{-2}$ $\Omega m^3$/kg; at study end 21.4±1.8*$10^{-2}$ $\Omega m^3$/kg, p<0.01) between the first stage (I) and the end of the second stage (II). These patients were considered to be at dry weight at that point. Comparison was made for all $DW_{cBIS}$-patients between the first stage (I) and the end of the second stage (II). Three $DW_{cBIS}$-patients had to be excluded in the analysis of the second stage (II) because of measurement errors.

1.a) wBIS for this group showed the following results: between the first stage (I) and the end of the second (II) mean post-hemodialytic weight was reduced by 2.3±0.8 kg (75.7±16.2 kg vs. 73.4±15.8 kg, p<0.001). The wECV as measured by wBIS decreased only by 1.1±1.0 L (13.8±2.5 L vs. 12.72±2.2 L, p<0.01) and thus accounted for only 46% of the actual weight loss. Despite the significant drop in wECV, the ratios of post-hemodialytic wECV/TBW (0.42±0.03 vs. 0.41±0.03, p=0.22) and wECV/wICV (0.72±0.08 vs. 0.69±0.08, p=0.24) did not change between the first stage (I) and the end of the second stage (II), respectively. Pre-hemodialytic but not post-hemodialytic wICV decreased from the first stage (I) to the end of the second stage (II).

Figure 10A:
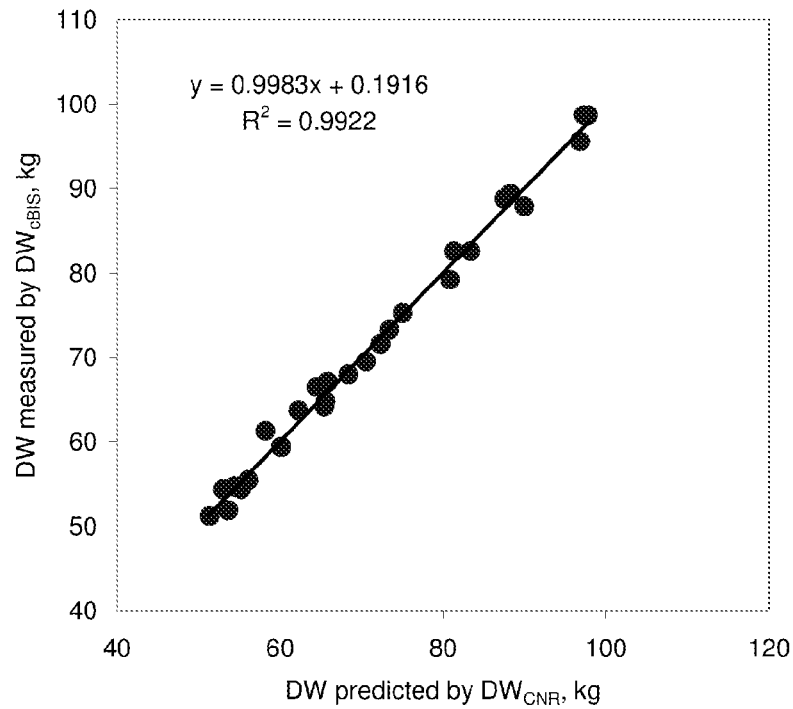
FIG. 10a is a correlation plot between $DW_{cBIS}$ and $DW_{CNR}$ for 27 patients.
Figure 10B:
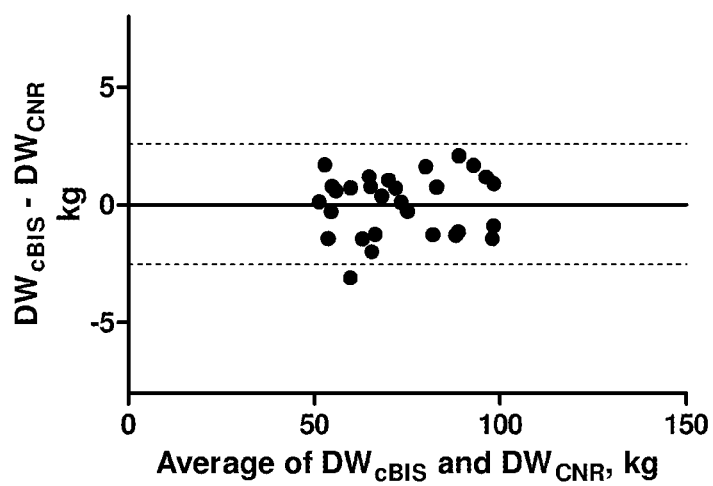
FIG. 10b is a Bland-Altman analysis for the data of FIG. 10a (difference in 0.025±1.3 kg).

1.b) Prediction of the normal fluid status weight ($NFSW_{wBIS}$) with the whole body model (WBM) showed significantly higher values for $NFSW_{wBIS}$ at all phases of fluid status than the actual $DW_{cBIS}$. The average prediction of $NFSW_{wBIS}$ in these patients decreased in parallel based on the current pre-hemodialytic weights representing different degrees of fluid status which were 1.8±1.2 kg, 1.4±1.0 kg, 1.0±1.2 kg during the first stage (I) and 0.59±1.3 kg at the second stage (II). $DW_{cBIS}$ and $NFSW_{wBIS}$ were highly correlated ($R^2$=0.996, p<0.001). Still, the mean difference between $DW_{cBIS}$ and $NFSW_{wBIS}$ measured at the dialysis session when $DW_{cBIS}$ was reached accounted to 1.96±1.04 kg. FIG. 1b shows the relationship between $NFSW_{wBIS}$ and $DW_{cBIS}$ at all stages of fluid overload. Furthermore, the normal fluid status weight predicted by WBM ($NFSW_{wBIS}$) decreased with progressive reduction of fluid overload. At the end of the study $NFSW_{wBIS}$ was 1.97±1.0 kg higher than $DW_{cBIS}$. Although $NFSW_{wBIS}$ and $DW_{cBIS}$ were highly correlated ($r^2$>0.99) in the $DW_{cBIS}$ group, this indicates that the dry weight of patients is lower than the NFSW predicted with wBIS. The results show that the amount of severe fluid overload is underestimated with wBIS. The correlation between the actual dry weight ($DW_{cBIS}$) defined by the cBIS method and the predicted dry weight ($DW_{CNR}$) employing calf normalized resistivity is shown in FIG. 10a. The result indicates that $DW_{CNR}$ is highly correlated ($R^2$=0.99) with $DW_{cBIS}$; see also the Bland-Altman analysis in FIG. 10b.

2) In the group of non-$DW_{cBIS}$-patients, the calf bioimpedance spectroscopy (cBIS) curves of R (t=0)/R (t) did not become essentially flat during a hemodialysis session and calf normalized resistivity increased only insignificantly from the first stage (I) (15.2±2.8*$10^{-2}$ $\Omega m^3$/kg) to the end of study (16.2±2.2*$10^{-2}$ $\Omega m^3$/kg) towards the threshold of the normal range (18-20*$10^{-2}$ $\Omega m^3$/kg). This indicates that these patients remained fluid overloaded despite fluid removal and therefore were grouped in the non-$DW_{cBIS}$-patients group.

2.a) wBIS for this group showed the following results: with a decrease in body weight of 1.9±1 kg (75.5±16.3 kg vs. 73.7±16.1 kg, p<0.001) wECV decreased 0.56±0.8 L (15.9±3.6 L vs. 15.4±3.6 L, p<0.05) which accounted for only 29% of the actual post-hemodialytic weight loss between the first stage (1) and the end of study. As noticed for the $DW_{cBIS}$-patients, post-hemodialytic ratios of wECV/TBW (0.46±0.07 vs. 0.46±0.05, p=0.74) and wECV/ICV (0.79±0.15 vs. 0.78±0.11, p=0.72) did not differ significantly between the first stage (I) and the end of study. To conclude, the results with respect to wBIS found in this group were similar to those obtained in the $DW_{cBIS}$-patients group. This means that wBIS is not adapted to determine the dry weight (DW) of a patient.

2.b) The predicted normal fluid status weight ($NFSW_{BIS}$) neither differed from the post-hemodialytic weight in the first stage (I) (74.9±17.2 kg vs. 75.5±16.3 kg, p=0.53) nor from the post-hemodialytic weight at the end of study (73.5±16.9 kg vs. 73.7±16.1 kg, p=0.86). However, $NFSW_{wBIS}$ in the first stage (I) at the beginning of the study (74.9±17 kg, p<0.01) was significantly higher than at the end of the first stage (I) (73.5±17 kg). This means, that the predicted value of $NFSW_{wBIS}$ does not give a reliable reference weight to which the fluid overload of a patient could be reduced. In fact, $NFSW_{wBIS}$ changes with the fluid status of the patient. To conclude, also $NFSW_{BIS}$ is not adapted to determine the absolute level of fluid status, to which the fluid overload of a patient should be reduced.

3) Blood pressures and number of hypotensive episodes: although in the $DW_{cBIS}$-patients group there was a trend towards higher levels of pre- and post-hemodialytic supine blood pressure at $NFSW_{wBIS}$, supine blood pressure did not significantly differ. Therefore, also the blood pressure cannot serve as an indication for the absolute level of fluid status corresponding to the dry weight, to which the fluid overload of a patient should be reduced.

4) Analysis with wBIS showed further that the $DW_{cBIS}$-group started with a pre-dialytic fluid status of +1.5±1.2 L (post-dialytic: −1.2±1 L) as compared to the normal fluid status. Therefore, in order to be able to adjust these patients on their dry weight, after a short period, all of these patients were monitored by cBIS, entering therefore the second stage (II) according to the present invention. At the end of the second stage (II) they had a pre-dialytic fluid status of 0.6±1.0 L (post-dialytic: −2.0±1.0 L).

The non-$DW_{BIS}$-patients group started with a pre-dialytic fluid status of 3.35±3.16 L (post-dialytic 0.6±3.2 L) as compared to the normal fluid status. Thus, these patients were by far in the first stage (I) according to the present invention at the beginning of the study. At the end of the study they still had a pre-dialytic fluid status of 3±2.88 L (post-dialytic 0.15±302 L). This indicates that these patients were still clearly in the first stage (I) at the end of the study. For them, the end of the study came too early for them to have reached the second stage (II) according to the present invention.

There are several reasons why the patients did not reach $DW_{cBIS}$: a higher degree of fluid overload at the start of the study, a lack of compliance with dietary salt and water prescriptions and/or a premature termination of the study after three months associated with patient discomfort.

CONCLUSION

One of the aims of dialysis treatment is to reduce the fluid overload of dialysis patients (in one embodiment by ultrafiltration). From the study, it becomes obvious that for severely fluid-overloaded patients (those comprised in the non-$DW_{cBIS}$-patients group), it would be advantageous to be monitored firstly by conventional methods with determination between dialysis sessions until a certain reduction of fluid overload with respect to the normal fluid status is achieved. From this point on, the patient can be adjusted to his/her dry weight using a method with determination of the fluid status during the sessions. This allows performing the adjustment of the patient precisely while avoiding discomfort to the patient induced by longer application-periods of intradialytic determination methods leading to non-compliance. One approach is to use intermittent measurement instead of continuous measurement in the early stages of intradialytic dry weight determination. This will improve comfort and patient compliance.

What is claimed is:

1. A method for estimating a dry weight of a dialysis patient comprising:
determining a current fluid status of the dialysis patient;
determining that the dialysis patient is in a first stage (I) if the current fluid status indicates a severe fluid overload;
determining that the dialysis patient is in a second stage (II) if the current fluid status indicates a fluid overload within a range of a normal fluid status;

determining a first fluid status of the dialysis patient between dialysis treatment sessions during the first stage (I);

determining a second fluid status of the dialysis patient during dialysis treatment sessions during the second stage (II), wherein the second fluid status is an intradialytic fluid status determined based on a continuously monitored evolution of a fluid status during a dialysis treatment session by at least one of a blood volume measurement method and segmental bioimpedance spectroscopy (BIS); and estimating the dry weight based on the second fluid status, the estimating comprising at least one of analysis of a resistance curve, a normalized resistivity, or a relative blood volume.

2. The method according to claim 1, wherein the first fluid status is determined by a pre-treatment session measurement.

3. The method according to claim 1, wherein the first fluid status is determined by a post-treatment session measurement.

4. The method according to claim 3, wherein the first fluid status is determined by at least one of:
a) a physical examination method,
b) an imaging method,
c) biochemical markers,
d) a thermal dilution determination method,
e) a bioimpedance measurement method,
f) the ratio between the total body water volume (TBW) and the extracellular water volume (ECV), and
g) a blood volume measurement method.

5. The method according to claim 1, further comprising estimating the normal fluid status based on the first fluid status.

6. The method according to claim 1, wherein the range of the normal fluid status comprises about 2.5 to about 0.25 L within an estimated normal fluid status of the dialysis patient.

7. The method according to claim 6, wherein the normal fluid status and/or weight ($NFSW_w$ms) is estimated by a whole body model or by a calf normalized resistivity (CNR) method.

8. The method according to claim 7, wherein the second stage (II) starts if a blood volume monitoring shows that the relative blood volume (RB V) decreases during a dialysis treatment session.

9. The method according to claim 1, wherein the first stage (I) lasts approximately 1 to 6 months.

10. The method according to claim 9, wherein the first fluid status is determined periodically.

11. The method according to claim 1, wherein the second fluid status is determined during every treatment session.

12. The method according to claim 1, wherein the dry weight of the dialysis patient is reached if a flattening of the resistance curve of the dialysis patient recorded during a treatment session in the second stage (II) is reached and/or the normalized resistivity of the dialysis patient is within a normal post-hemodialytic range of a comparison group.

13. The method according to claim 12, wherein the resistance is measured by calf bioimpedance spectroscopy and/or the normalized resistivity of the dialysis patient is the normalized calf resistivity.

14. The method according to claim 1, wherein the severe fluid overload comprises a fluid overload greater than about 2.5 liters to about 0.2 liters of an estimated normal fluid status of the dialysis patient.

15. The method according to claim 1, wherein the first fluid status is an interdialytic fluid status determined based on an intermittent measurement.

16. The method according to claim 15, wherein the intermittent measurement is determined by a non-continuous measurement without electrodes on the patient.

17. The method according to claim 15, wherein the intermittent measurement does not include a blood volume measurement method or segmental bioimpedance spectroscopy (BIS).

18. An apparatus, comprising
at least one processor; and
a memory coupled to the at least one processor, the memory comprising instructions that, when executed by the at least one processor, cause the at least one processor to:
receive a first fluid status of a dialysis patient during a first stage (I), wherein the dialysis patient is in the first stage (I) if a current fluid status indicates a severe fluid overload, the first fluid status comprising an interdialytic fluid status measured using an intermittent measurement method,
receive a second fluid status of the dialysis patient during a second stage (II), wherein the dialysis patient is in second stage (II) if the current fluid status indicates a fluid overload within a range of a normal fluid status, the second fluid status comprising an intradialytic fluid status measured using an continuous measurement method during a dialysis session, and
estimating the dry weight based on the second fluid status.

19. The apparatus according to claim 18, the instructions, when executed by the at least one processor, cause the at least one processor to determine a dosage of at least one of a medicament, an antibiotic, and a parenterally-administered drug based on at least one of the first fluid status and the second fluid status.

20. The apparatus according to claim 18, the instructions, when executed by the at least one processor, cause the at least one processor to estimate the normal fluid status based on the first fluid status.

21. The apparatus according to claim 18, wherein the severe fluid overload comprises a fluid overload greater than about 2.5 liters to about 0.2 liters of an estimated normal fluid status of the dialysis patient.

22. The apparatus according to claim 18, wherein the range of the normal fluid status comprises about 2.5 to about 0.25 L within an estimated normal fluid status of the dialysis patient.

23. The apparatus according to claim 18, wherein the second stage (II) starts if a blood volume monitoring shows that the relative blood volume (RB V) decreases during a dialysis treatment session.

* * * * *